United States Patent
Chin et al.

(10) Patent No.: US 6,197,599 B1
(45) Date of Patent: Mar. 6, 2001

(54) METHOD TO DETECT PROTEINS

(76) Inventors: Guorong Chin, 165 Edwards St., New Haven, CT (US) 06511; Yingyi Wang, 2 Elizabeth St., Apt. #2, West Haven, CT (US) 06516

(*) Notice: Subject to any disclaimer, the term of this patent is extended or adjusted under 35 U.S.C. 154(b) by 0 days.

(21) Appl. No.: 09/126,483

(22) Filed: Jul. 30, 1998

(51) Int. Cl.$^7$ ............... A61B 5/055; A61K 39/395; G01N 33/53; C07K 16/00

(52) U.S. Cl. ............ 436/518; 424/9.34; 424/134.1; 435/7.1; 435/7.8; 435/7.9; 435/7.92; 435/970; 435/971; 435/973; 435/975; 436/807; 524/900; 530/387.3

(58) Field of Search .............. 424/9.34, 134.1; 435/7.1, 7.8, 7.9, 7.92, 970.971, 973, 975; 436/807; 524/900; 530/387.3

(56) References Cited

U.S. PATENT DOCUMENTS

| | | | |
|---|---|---|---|
| 4,274,832 | * | 6/1981 | Wu et al. ........................... 23/230 |
| 5,001,072 | * | 3/1991 | Olson ............................. 436/500 |
| 5,283,173 | * | 2/1994 | Fields et al. ........................ 435/6 |
| 5,451,504 | * | 9/1995 | Fitzpatrick et al. ................ 435/7.2 |
| 5,567,627 | * | 10/1996 | Lehnen ............................. 436/518 |

FOREIGN PATENT DOCUMENTS

| | | | | |
|---|---|---|---|---|
| 461462 | * | 12/1991 | (EP) | ............. G10N/33/543 |
| WO 96/10747 | * | 4/1996 | (EP) | ............. G01N/33/543 |

OTHER PUBLICATIONS

Phizicky et al. 1995. Microbiological Reviews. 59(1):94–123.*

* cited by examiner

Primary Examiner—James C. Housel
Assistant Examiner—Ja-Na A. Hines

(57) ABSTRACT

A device comprises a solid support and multiple immobilized agents for protein detection is described. The immobilized agents are mainly proteins, such as antibodies and recombinant proteins. The immobilized agents can be synthesized peptides or other small chemicals. Agents are individually deposited in a predetermined order, so that each of the agents can be identified by the specific position it occupies on the support. The immobilized agents on the solid support retain their protein binding capability and specificity. Methods employing the device are extremely powerful in screening protein expression patterns, protein posttranslational modifications and protein—protein interactions.

16 Claims, 2 Drawing Sheets

METHOD TO DETECT PROTEINS

BACKGROUND

This invention relates generally to the field of protein detection.

Proteins are the major components of cells. They determine the shape, structure, and function of the cell. Proteins are assembled by 20 different amino acids each with a distinct chemical property. This variety allows for enormous versatility in the chemical and biological properties of different proteins. Human cells have about 100,000 genes for encoding different proteins. Despite the fact that new proteins are being discovered at an unprecedented rate, protein structure and function studies are lagging behind, mainly due to a lack of high throughput methods.

Antibodies and recombinant proteins are powerful tools for protein studies. Antibodies are a large family of glycoproteins that specifically bind antigens. A protein can be identified by its specific antibodies in immunochemical methods such as Western blot, immunoprecipitation, and enzyme linked immunoassay. Monoclonal and polyclonal antibodies against most known proteins have been generated and widely used in both research and therapy. Genes can be readily expressed in organisms like bacteria and yeast and this has made recombinant proteins convenient and indispensable tools in protein structure and function studies. There is a growing demand for recombinant proteins, especially in large scale screening of drug targets and in clinical medicine. Today, numerous antibodies and recombinant proteins have been produced. One important issue is how to analyze proteins in large scale by using a large number of antibodies or recombinant proteins in a single experiment.

It is often necessary to immobilize proteins on a solid support during the process of studying proteins. In Western blot analysis, proteins of interest are first separated by electrophoresis and then transferred and immobilized onto a nitrocellulose or a polyvinylidene difluoride (PVDF) membrane. In the phage display screening of a protein expression library, several hundred thousand proteins expressed by phages are immobilized on membranes. In both Western blotting and phage display screening, proteins are immobilized non-covalently. The protein of interest is then selected by its unique property, i.e., interaction with an antibody. In some other applications such as immunoprecipitation and affinity purification, agents (e.g., antibodies, ligands) are covalently conjugated onto solid supports (e.g., agarose beads) through their primary amines, sulfhydryls or other reactive groups. In general, proteins retain their abilities of interacting with other proteins or ligands after immobilization.

Monitoring the expressions and properties of a large number of proteins is desired in many important applications. One such application is to reveal protein expression profiles. A cell can express a large number of different proteins. And the expression patterns (the number of proteins expressed and the expression levels) vary in different cell types. This difference is the primary reason that different cells have different functions. Since many diseases are caused by the change in protein expression pattern, comparing protein expression patterns between normal and disease conditions may reveal proteins whose changes are critical in causing the disease and thus identify appropriate therapeutic targets. Methods of detecting protein expression profiles will also have other important applications including tissue typing, forensic identification, and clinical diagnosis. Protein expression pattern can be examined with antibodies in an immunoassay, but usually in a small scale. Therefore, one major obstacle in profiling protein expression pattern is a lack of large scale protein screening methods.

Protein posttranslational modifications (e.g., phosphorylation, glycosylation, and ubiquitination) play critical roles in regulating protein activity. One of the modifications is phosphorylation at either serine, threonine or tyrosine residues. Protein phosphorylation is an important mechanism in signal transduction. Aberrant protein phosphorylation contributes to many human diseases. Among the methods of detecting protein phosphorylation, metabolic labeling of cells with radioisotopes and immuno-detection of phosphoproteins with antibodies are the most commonly used. However, these methods are only applicable to analyzing one or several proteins each time. Antibodies specific for phosphorylated amino acids, such as PY20, can reveal multiple phosphorylated proteins, but fail to identify them. A new method for simultaneously detecting and identifying multiple phosphorylated proteins is highly desirable for signal transduction studies and clinical diagnosis.

Protein-protein interaction is an important way by which a protein carries out its function(s). Currently, there are several methods to detect protein—protein interactions. Among them, co-immunoprecipitation (Harlow and Lane, 1988, Antibodies, a laboratory manual. Cold Spring Harbor Laboratory), yeast two-hybrid screening (Fields and Song, 1989, Nature, 340:245–246) and phage display library screening (Smith, 1985, Science 228:1315–1317) are the most commonly used. However, there are severe limitations in these methods. In co-immunoprecipitation, a protein of interest can be precipitated with its antibody which is immobilized on agarose beads. Any other protein(s) that co-immunoprecipitated with the protein of interest can be identified by either blotting with its antibody when it is known or purification and sequencing when it is a novel protein. However, this method can not be applied to large scale identification of protein—protein interactions. Yeast two-hybrid screening is a recently developed technique for detecting protein—protein interaction. Although a single yeast two-hybrid screening assay can detect many interacting proteins, it is time-consuming and prone to false positive results. Moreover, many protein—protein interactions only occur in the presence of additional cellular factors or after posttranslational modifications, which may not be present in yeast. Therefore, yeast two-hybrid screening fails to identify many important protein—protein interactions that only take place in mammalian cells. Phage display screening of protein—protein interaction suffers similar limitations.

Therefore, there is a need for improved techniques which allow rapid and detailed analysis of multiple proteins for both basic research and clinical medicine. Such techniques will be extremely valuable in monitoring the overall patterns of protein expression, protein posttranslational modification, and protein—protein interaction in different cell types or in the same cell type under different physiological or pathological conditions.

SUMMARY

We have designed a device (protein array) which has many agents immobilized on a solid support. Agents are immobilized in a predetermined order, i.e., each agent is immobilized at a specific position so that it can be identified by its unique position on the support. The device can capture and identify the specific proteins from a mixture (e.g., cell lysate). After capture and separation, the proteins can be further characterized. Therefore, protein array makes it possible to study a wide variety of proteins in a single experiment by a large number of antibodies and/or recombinant proteins immobilized on a support.

Protein array and the methods presented here have several significant advantages over the current methods. First, protein array allows rapid detection of many proteins and thus makes it possible to compare protein expression profiles from different sources or those from the same source but under different conditions. Information on protein expression profile is very useful in identifying diagnostic and therapeutic targets. Second, protein array makes it possible to detect posttranslational modifications of numerous proteins and provide a valuable tool to investigate protein and cellular regulations. Third, it can screen a large number of potential interactions directly; and it can detect interactions that take place only under certain conditions, e.g. phosphorylation. Protein array is therefore useful for a variety of applications, particularly for revealing disease mechanisms, searching for diagnostic indicators and for identifying therapeutic targets. In addition, protein array allows an individual user to access a large number of immobilized antibodies or recombinant proteins.

DESCRIPTION OF THE PREFERRED EMBODIMENTS

Figure 1:
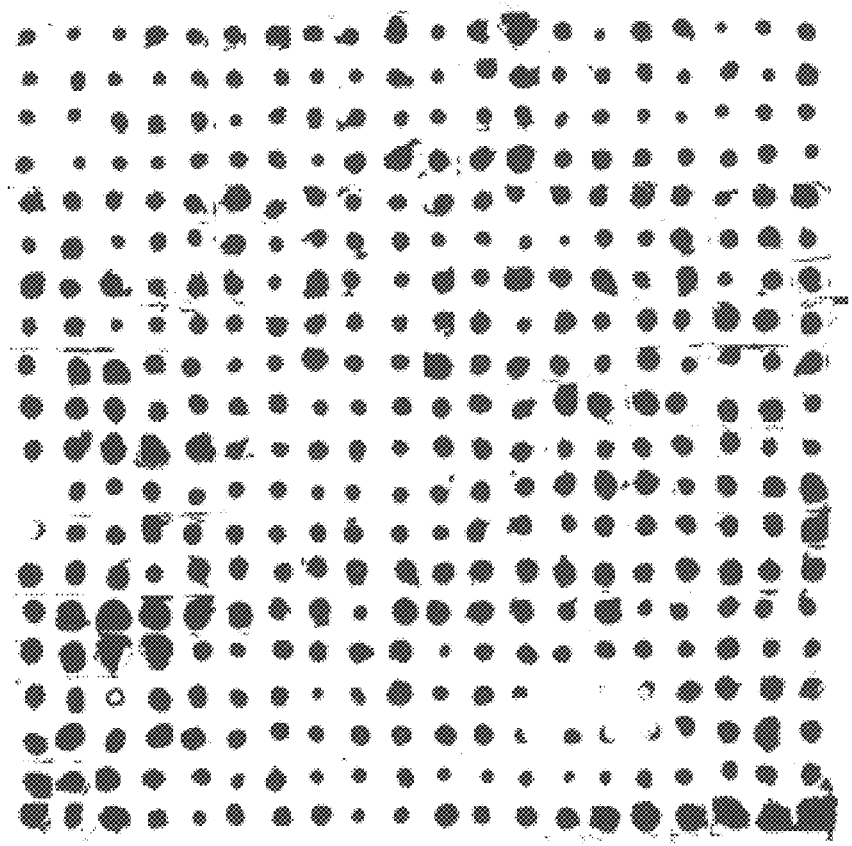
FIG. 1 shows an example of protein array comprising a PVDF membrane as the solid support and 400 different antibodies immobilized on the membrane.

The present invention (protein array) provides a powerful and quantitative tool for determining protein expression patterns, protein posttranslational modifications and protein—protein interactions. Protein array is based on several principles. First, a protein can be recognized and identified unambiguously by specific molecules such as antibodies, recombinant proteins and small chemicals that can specifically interact with it. Second, a protein or a small chemical can be immobilized on a solid support and the immobilized molecule still retains its ability in protein—protein interaction. Agents (antibodies, recombinant proteins, and small chemicals) can be immobilized on solid supports such as glass plates, agarose beads, or PVDF membranes (LeGendre, 1990, BioTechniques, Vol.9, No.6, p. 788–805). Third, many different agents can be immobilized at different positions on a solid support without cross interactions among them. This insures that each agent independently interacts with its respective target protein.

The term "agents" as used herein refers to antibodies, recombinant proteins, synthesized peptides, and other chemicals immobilized on the solid support of a protein array.

In the preferred embodiments, the agents immobilized on a solid support can be antibodies, recombinant proteins, or small chemicals. Antibodies are raised by immunizing animals (e.g., rabbit, mouse, rat, goat or chicken) with antigens (proteins or peptides). A large number of antibodies (monoclonal and polyclonal) are commercially available.

Recombinant proteins are constructed by using recombinant DNA techniques. Many proteins have been conveniently expressed in a recombinant form with a tag such as glutathione-S-transferase (GST) and polyhistidine (6xHis), to facilitate purification and identification. Small chemicals (including but not limited to synthesized peptides) can be immobilized on a support to capture and identify specific proteins.

The term "supports" as used herein refers to the materials on which agents are deposited and immobilized.

In the preferred embodiments, the supports are either plates (glass or plastics) or membranes made of nitrocellulose, nylon, or polyvinylidene difluoride (PVDF). Membranes are easier to handle and agents can be readily immobilized on them. Glass or plastic plates provide rigid support and are therefore necessary in some special applications.

Agents are immobilized on a solid support directly or indirectly. Agents can be directly deposited at high density on a support, which can be as small as a microscopic slide. Similar technology was developed for making high density DNA microarray (Shalon et al., Genome Research,1996 Jul; 6(7): 639645.). Agents can also be immobilized indirectly on the support. For instance, protein A or G can be printed on a support. Agents (antibodies) are then immobilized on the support through their interactions with protein A or G. The advantage of this method is that by engaging the constant regions of antibodies with protein A or G, the variable regions of the antibodies (antigen-binding domains) will be fully exposed to interact with antigens. Recombinant fusion proteins can be immobilized through the interaction between their tags and the ligands printed on the support. One most important characteristic of protein arrays is that all agents are immobilized at predetermined positions, so that each agent can be identified by its position. After agents are immobilized, the support can be treated with 5% non-fat milk or 5% bovine serum albumin for several hours in order to block non-specific protein binding.

Different protein arrays can be made for different purposes. For instance, "Cytokine Array" can be made of agents for cytokine assay. "Cell Cycle Array" can be made of agents for detecting cell cycle related factors; "Signal Transduction Array" can be made of agents for examining signaling proteins; and "Transcription Factor Array" can be made of agents for analyzing activators and suppressors of transcription. In order to reveal the broad protein expression pattern in a source (e.g. a cell line), thousands of different antibodies are immobilized in a single support. The amount of antibodies immobilized can also be different, preferably in the range of nanogram to microgram. The number of different agents immobilized on one solid support varies depending on the particular applications.

Protein array can be applied in studying protein expression patterns. An antibody array is incubated with a protein sample prepared under the conditions that native protein—protein interactions are minimized. After incubation, unbound or non-specific binding proteins can be removed with several washes. Proteins specifically bound to their respective antibodies on the array are then detected. Because the antibodies are immobilized in a predetermined order, the identity of the protein captured at each position is therefore known. Measurement of protein amount at all positions on the array thus reflects the protein expression pattern in the sample. The quantities of the proteins trapped on the array can be measured in several ways. First, the proteins in the samples can be metabolically labeled with radioactive isotopes (S-35 for total proteins and P-32 for phosphorylated proteins). The amount of labeled proteins bound to each antibody on an array can be quantitated by autoradiography and densitometry. Second, the protein sample can also be labeled by biotinylation in vitro. Biotinylated proteins trapped on the array will then be detected by avidin or streptavidin which strongly binds biotin. If avidin is conjugated with horseradish peroxidase or alkaline phosphatase, the captured protein can be visualized by enhanced chemical luminescence. The amount of proteins bound to each antibody represents the level of the specific protein in the sample. If a specific group of proteins are interested, they can be detected by agents which specifically recognize them. Other methods, like immunochemical staining, surface plasmon resonance, matrix-assisted laser desorption/ionization-time of flight, can also be used to detect the captured proteins.

Protein array can be applied in studying posttranslational modifications such as phosphorylation, glycosylation or ubiquitination. In the preferred embodiments, arrays comprising antibodies on glass plates or membranes are used to capture cellular proteins. The phosphorylation of the proteins captured on the array can be revealed if the proteins are metabolically labeled with P-32 in vivo. Alternatively, the phosphorylation can be detected by antibodies against phosphorylated amino acids. Antibodies against phosphotyrosine, phosphoserine or phosphothreonine are commercially available and used in many applications. When these antibodies are used, the phosphorylation state of a protein can be detected through a similar strategy used in Immunoblotting. Similarly, the glycosylation of the many proteins captured on the array can be studied either by labeling glycoproteins with radioactive glycosylation precursors or by using molecules that specifically recognize carbohydrate moieties of glycoproteins. A family of such molecules are lectins including Concanavalin A and Wheat Germ agglutinin. To detect protein ubiquitination, antibodies specific for ubiquitin can be used.

Figure 4:
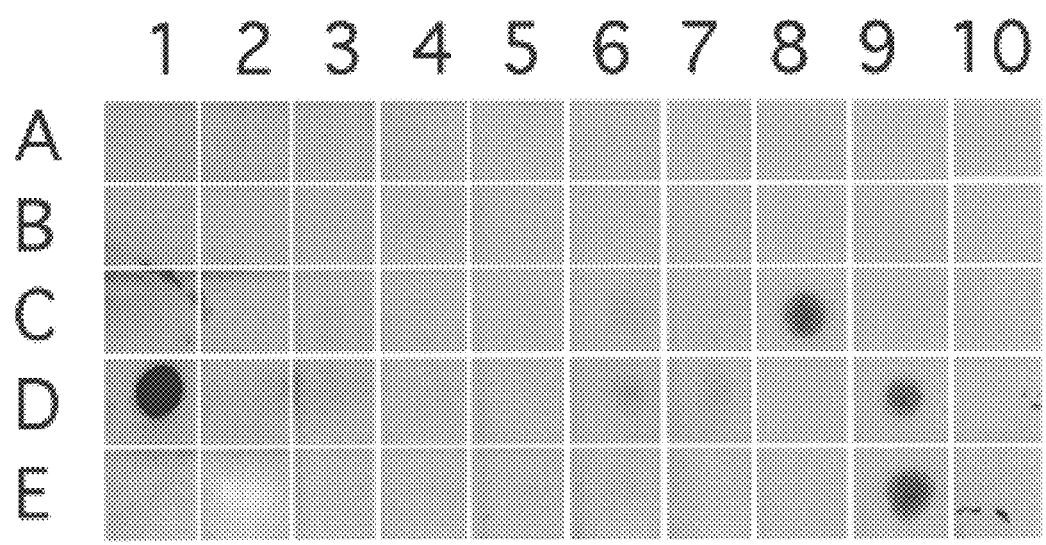
FIG. 4 shows the use of protein array to identify protein—protein interactions.

Protein array can be applied in studying protein—protein interactions. When a protein is captured by its antibody immobilized on an array, other proteins may also be tethered to the same position due to protein—protein interaction. A protein mixture (e.g., cell lysate) is made under such conditions that protein—protein interactions are preserved. After incubation of the protein mixture with the array, the protein of interest will be captured to the position where its interacting protein(s) is captured. By localizing the position of the interested protein, the identity of its interacting protein is known (because the identity of each agent is predetermined). The protein of interest can be localized by either its specific antibodies or other methods. The protein of interest can be expressed as a fusion protein with a tag and can then be detected by the tag's specific property. For example, a GFP fusion protein can be readily detected under UV light. FIG. 4 shows an example of how to use this technique. It is worth to note that one protein can interact with more than one protein and may interact with different proteins under different conditions. Besides, using an array with a larger pool of different agents will increase the chance of detecting the interacting proteins.

In another preferred embodiment, protein arrays made of multiple recombinant proteins are used to identify protein—protein interactions. Many recombinant fusion proteins containing a tag (e.g., GST or 6xHis) at their N- or C- terminus are constructed, expressed, and purified. These recombinant proteins are immobilized as agents onto the support printed with their ligands (e.g., glutathione or nickel). After incubation, the protein of interest is captured by the agents (recombinant proteins) immobilized on the array. By detecting the position where the protein of interest is captured, the identity of its interacting protein is obtained. The recombinant protein array provides a very convenient tool for detecting protein—protein interaction.

As evident in the above description, protein array has broad applications. It allows one to compare protein expression patterns, protein posttranslational modification, and protein—protein interactions between two types of cell, tissue, or patient specimen. Therefore, it will be an extremely useful tool in clinical diagnosis and new drug search. Only time will reveal its full potential.

EXAMPLES

For exemplary purpose, we chose PVDF membrane as the support and manually deposited antibodies on it. After 10 minutes incubation, all antibodies became immobilized. The number of antibodies immobilized on the array varied depending on the applications and the amount of antibodies immobilized was in the range of 0.1 microgram to 1.0 microgram. After immobilization, the membranes were incubated with 5% non-fat milk or 5% BSA for 2 hours in order to saturate their binding capacity and block non-specific protein binding. By using the protein array made in this way, cell lysates prepared from different cell lines were analyzed for protein expression, protein tyrosine phosphorylation, and protein—protein interaction.

Example 1

An example of protein array is shown in FIG. 1. In this array, 400 different antibodies (about 0.1 microgram each) were deposited and immobilized on a PVDF membrane, each at a predetermined position. Each position corresponded to only one kind of antibody. The immobilized agents on the membrane are invisible. To confirm the antibodies were indeed immobilized on the support stably, the array was incubated with alkaline phosphatase-conjugated secondary antibody for 1 hour at room temperature followed by three washes. Then the chromogenic substrate of alkaline phosphatase was applied and insoluble color product was yielded at the positions where antibodies were immobilized.

Example 2

Figure 2:
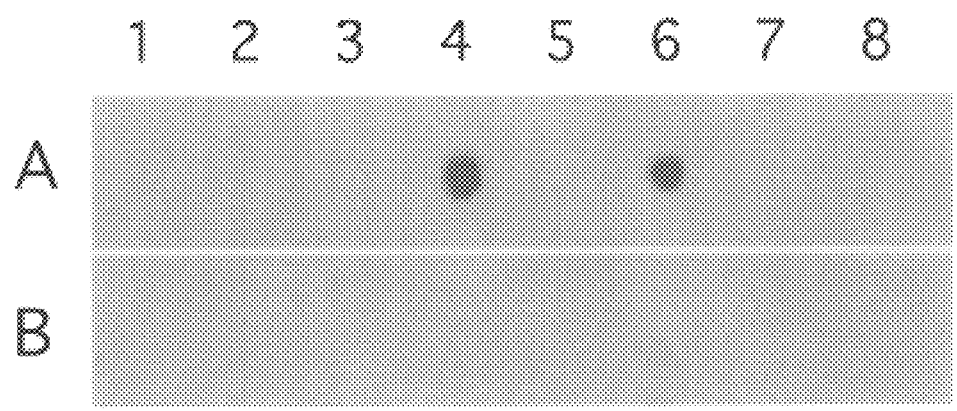
FIG. 2 shows the use of protein array to capture and separate proteins and to compare protein expression patterns between two sources.

Protein array can be used to detect protein expression profiles. A gap junctional channel protein Connexin 43 (Cx43) conjugated with a green fluorescent protein (GFP) was overexpressed in HeLa cells and detected by protein arrays. GFP emits fluorescent light upon excitation and thus allows the identification of a GFP-fusion protein by laser scanner. The antibodies against GFP, Cx43, and some other cellular proteins were immobilized on PVDF membranes. Cell lysates prepared from HeLa cells transfected with GFP-Cx43 or a control vector were incubated with two identical antibody arrays, respectively. After 2 hours of incubation, unbound proteins were removed by three washes. The membrane was then examined with a laser scanner. As shown in FIG. 2, the signal can only be detected in array A which was incubated with the lysate containing the fusion protein but not in array B which was incubated with the control cell lysate. Furthermore, in FIG. 2A, the fusion protein was only detected by the antibodies for either GFP or Cx43 (antibody at position 4 was specific for GFP and antibody at position 6 was specific for Cx43). This example illustrates the examination of the expression of one protein. However, many proteins can be simultaneously examined with an array comprising a large number of immobilized antibodies. This example also indicates that multiple antibodies can recognize their corresponding antigens independently without cross reactions.

Example 3

Figure 3:
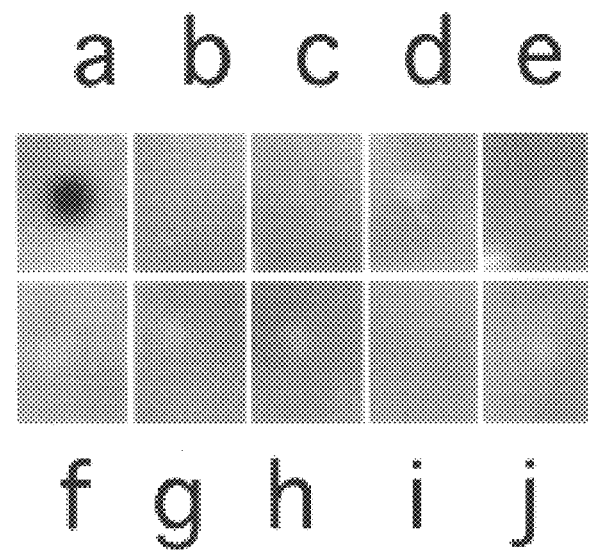
FIG. 3 shows the use of protein array to detect protein tyrosine phosphorylation.

Protein array can be used to detect protein posttranslational modifications (e.g., protein phosphorylation, glycosylation and ubiquitination). We demonstrate here the use of a protein array in detection and identification of protein tyrosine phosphorylation. Similar approaches can be used to study protein serine/threonine phosphorylation. We used a PVDF membrane immobilized with agents including rabbit polyclonal antibodies (1 microgram each) against epidermal growth factor (EGF) receptor, Connexin 43, N-cadherin, and some others. The membrane was blocked for 2 hours in 5% BSA. Lysates prepared from EGF-treated HeLa cells were incubated with the membrane for 2 hours. The array was then incubated with horseradish peroxidase-linked phosphotyrosine antibody (PY20) followed by enhanced chemiluminescence (ECL) detection. As shown in FIG. 3, a signal was detected only at the position where EGF receptor antibody was immobilized (position a), suggesting EGF receptor was autophosphorylated in HeLa cells treated with EGF. After a longer exposure, some positions immobilized with other antibodies also showed signals, suggesting proteins trapped at these positions are also tyrosine phosphorylated. More phosphorylated proteins can be detected and identified simultaneously with an array comprising a large number of immobilized antibodies.

Example 4

Protein array can be used to detect protein—protein interactions. We demonstrate here the use of a protein array in detection and identification of proteins that interact with c-Fos. Fifty antibodies were immobilized on a PVDF membrane (about 0.5 microgram each). The array was blocked with 5% non-fat milk for 2 hours and incubated for another 2 hours with the cell lysate prepared under non-disruptive condition (1% Triton in phosphate-buffered saline). After incubation, the membrane was washed 3 times with PBS. The membrane was then incubated with horseradish peroxidase-linked c-Fos antibody followed by ECL detection. As seen in FIG. 4, ECL signal was detected at several positions, i.e., C8, D1, D9, and E9, suggesting c-Fos was co-immunoprecipitated with those proteins specifically recognized by their corresponding antibodies immobilized at the respective positions.

The device of the invention provides a convenient, economic vehicle to disseminate antibodies, recombinant proteins and other precious reagents. The methods employing the device are extremely powerful in studying disease mechanisms, screening drug targets, and investigating protein and cell functions. Although the invention has been described with reference to the presently preferred embodiments, one should keep in mind that various modifications can be made without departing from the spirit of the invention. For example, protein array can be used to screen small chemicals for their protein binding properties and potential use as drugs. Protein array can also be used to detect viruses and cells which express molecules interacting with agents immobilized on the support. Accordingly, the scope of the invention should be determined not by the embodiment(s) illustrated but by the following claims and their legal equivalents.

What is claimed is:

1. A method for identifying an interactions between a single first test protein and one or more of a plurality of different second test proteins, said method comprising the steps of:

immobilizing a plurality of antibodies on a solid support, wherein a different antibody directed against each of said second test proteins is provided at known, predetermined positions on said support such that each of said antibodies can be identified by the position where it is immobilized;

preparing a mixture containing said first test protein and said plurality of second test proteins under conditions to permit interaction between said first test protein and said second test protein to occur;

applying said mixture to said solid support with immobilized antibodies and incubating under conditions to permit binding of said second test proteins thereto;

detecting the positions of said first test protein on said solid support thereafter;

identifying the second test protein from the positions where said first test protein is detected, whereby the interaction between said first test protein and the one or more of said second test proteins is identified.

2. A method for identifying unknown interactions between a first test protein and one or more of a plurality of different second test proteins, said method comprising the steps of:

immobilizing a plurality of antibodies on a solid support, wherein a different antibody directed against each of said second test proteins is provided at known, predetermined positions on said support such that each of said antibodies can be identified by the position where it is immobilized;

preparing a mixture containing said first test protein and said plurality of second test proteins under conditions to permit interaction between said first test protein and said second test protein to occur;

applying said mixture to said solid support with immobilized antibodies and incubating under conditions to permit binding of said second test proteins thereto;

detecting the positions of said first test protein on said solid support thereafter;

identifying the second test protein from the positions where said first test protein is detected, whereby the interaction between said first test protein and the one or more of said second test proteins is identified.

3. A method for identifying an interactions between a single first test protein and one or more of a plurality of different second test proteins, said method comprising the steps of:

immobilizing a plurality of antibodies on a solid support, wherein a different antibody directed against each of said second test proteins is provided at known, predetermined positions on said support such that each of said antibodies can be identified by the position where it is immobilized;

preparing a mixture containing said plurality of second test proteins;

applying said mixture to said solid support with immobilized antibodies and incubating under conditions to permit binding of said second test proteins thereto;

applying said first test protein to said solid support with immobilized antibodies and incubating under conditions to permit binding of said first test protein to said second test proteins;

detecting the positions of said first test protein on said solid support thereafter;

identifying the second test protein from the positions where said first test protein is detected, whereby the interaction between said first test protein and the one or more of said second test proteins is identified.

4. A method for identifying unknown interactions between a first test protein and one or more of a plurality of different second test proteins, said method comprising the steps of:

immobilizing a plurality of antibodies on a solid support, wherein a different antibody directed against each of said second test proteins is provided at known, predetermined positions on said support such that each of said antibodies can be identified by the position where it is immobilized;

preparing a mixture containing said plurality of second test proteins;

applying said mixture to said solid support with immobilized antibodies and incubating under conditions to permit binding of said second test proteins thereto;

applying said first test protein to said solid support with immobilized antibodies and incubating under conditions to permit binding of said first test protein to said second test proteins;

detecting the positions of said first test protein on said solid support thereafter;

identifying the second test protein from the positions where said first test protein is detected, whereby the interaction between said first test protein and the one or more of said second test proteins is identified.

5. The method of claim 1 to 4, wherein none of said first test protein and said second test proteins are antibodies.

6. The method of claim 1 to 4, wherein the positions of said first test protein are detected with antibodies against said first test protein.

7. The method of claim 1 to 4, wherein the positions of said first test protein are detected by mass spectrometry.

8. The method of claim 1 to 4, wherein said first test protein is a fusion protein with a detectable tag.

9. The method of claim 8, wherein said tag is a fluorescent protein.

10. The method of claim 1 to 4, wherein said first test protein is an antibody specific for a phosphorylated amino acid.

11. The method of claim 10, wherein said amino acid is a tyrosine.

12. The method of claim 1 to , wherein said first test protein is a lectin.

13. The method of claim 1 to 4, wherein said support is made of materials selected from the group consisting of nitrocellulose, nylon, polyvinylidene difluoride, glass, or plastics, and their derivatives.

14. The method of claim 1 to 4, wherein said mixture is cell lysate prepared from prokaryotic or eukaryotic cells.

15. The method of claim 1 to 4, wherein the number of said antibodies immobilized on said solid support ranges from 100 to 10,000 different kinds.

16. The method of claim 1 to 4, wherein the number of said antibodies immobilized on said solid support ranges from 500 to 5,000 different kinds.

* * * * *

UNITED STATES PATENT AND TRADEMARK OFFICE
CERTIFICATE OF CORRECTION

PATENT NO. : 6,197,599 B1
DATED : March 6, 2001
INVENTOR(S) : Yingjian Wang, Yue Eugene Chin and Yingyi Wang It is certified that error appears in the above-identified patent and that said Letters Patent is hereby corrected as shown below:

<u>Claim 3,</u>
"The method of claim 1 to, wherein said first test protein is a lectin." should read
-- The method of claim 1 to 4, wherein said first test protein is a lectin. --

Signed and Sealed this

Nineteenth Day of March, 2002

Attest:

JAMES E. ROGAN
*Director of the United States Patent and Trademark Office*

*Attesting Officer*